United States Patent [19]
Wilson et al.

[11] Patent Number: 5,496,553
[45] Date of Patent: Mar. 5, 1996

[54] METHODS AND COMPOSITIONS FOR THE TREATMENT OF NIDDM

[75] Inventors: Bary W. Wilson, Kennewick; James A. Campbell, Pasco; Lyle B. Sasser, Richland, all of Wash.; Patricio Hortal, Mar del Plata, Argentina

[73] Assignee: Battelle Development Corporation, Richland, Wash.

[21] Appl. No.: 300,927

[22] Filed: Sep. 2, 1994

Related U.S. Application Data

[63] Continuation of Ser. No. 965,904, Oct. 22, 1992, abandoned, which is a continuation of Ser. No. 596,169, Oct. 11, 1990, abandoned, which is a continuation-in-part of Ser. No. 420,266, Oct. 12, 1989, abandoned, which is a continuation-in-part of Ser. No. 180,420, Apr. 12, 1988, abandoned.

[51] Int. Cl.$^6$ ..................................................... A61K 35/78
[52] U.S. Cl. ................................ 424/195.1; 435/240.25; 435/240.47; 435/240.48; 514/866
[58] Field of Search ..................... 424/198.1; 514/866, 514/53, 54, 25; 536/22.1, 55.1, 55.2, 55.3; 435/240.45, 240.47, 240.48

[56] References Cited

U.S. PATENT DOCUMENTS 4,228,274  10/1980  Ponpipom et al. .................... 536/22
4,696,919  9/1987  Itnohara et al. ....................... 514/62

FOREIGN PATENT DOCUMENTS 2465484  4/1981  France ........................... A61K 35/78

OTHER PUBLICATIONS

Bonsal, et al., Intian J. Biochem & Biophys 18: 377, 1981.
Hikino, et al., Int. J. Crude Drug Res. 24: 183, 1986.
Hikino, et al., Planta Medica, 1986 pp. 490–492.
Srivastava et al., Int. J. Crude Drug Res. 24: 177–176, 1986.
Jimenez, et al., Planta Medica, 1986, pp. 260–262.
Lewis et al., Medicina Botany: Plants Affecting Man's Health, Welegrson pp. 213–220, 1977.

*Primary Examiner*—John W. Rollins
*Attorney, Agent, or Firm*—Seed and Berry

[57] ABSTRACT

A variety of hypoglycemic agents and compositions for use in the maintenance of maturity onset non-insulin dependent diabetes mellitus (NIDDM) are disclosed. The present invention also discloses methods for reducing the blood glucose level in a patient, as well as methods for reducing symptomatic conditions associated with diabetes in a patient.

36 Claims, No Drawings

METHODS AND COMPOSITIONS FOR THE TREATMENT OF NIDDM

CROSS-REFERENCE TO RELATED APPLICATION

This application is a continuation of U.S. application Ser. No. 07/965,904, filed Oct. 22, 1992, now abandoned; which is a continuation of U.S. application Ser. No. 07/596,169, filed Oct. 11, 1990, now abandoned; which is a continuation-in-part of U.S. Ser. No. 07/420,266, filed Oct. 12, 1989, now abandoned; which is a continuation-in-part of U.S. Ser. No. 07/180,420, filed Apr. 12, 1988, now abandoned.

TECHNICAL FIELD

The present invention is generally directed toward the treatment of maturity onset non-insulin dependent diabetes mellitus (NIDDM), and more specifically, to the management of NIDDM through the use of hypoglycemic agents.

BACKGROUND OF THE INVENTION

Maturity onset non-insulin dependent diabetes mellitus (NIDDM) and associated preclinical conditions, such as insufficient glucose tolerance (IGT), are characterized by the diminished capacity of islet cells of the pancreas to synthesize and release sufficient insulin in response to rising blood glucose levels. Decreased sensitivity to insulin in peripheral tissues of many diabetics is also observed. New case reports of NIDDM and IGT appear to be increasing at an accelerating rate in several Western countries (Zimmer and King, *World Trends in Diabetes Epidemiology,* 1986). In the United States, for example, it is estimated that approximately five percent of the adult population suffers from some form of diabetic condition, with the rate of new cases increasing at about six percent per year, or approximately 600,000 new cases each year. An additional, not well-defined population exhibits preclinical symptoms such as IGT.

The management of NIDDM requires special dietary measures, and often the use of a pharmaceutical hypoglycemic agent. These agents have the ability to stimulate insulin production in the islet cells and, in conjunction with dietary measures, can help to stabilize blood sugar levels.

There are currently two chemically distinct families of oral hypoglycemic agents used in the management of NIDDM. One such family of agents, the biguanides, have been largely withdrawn from the commercial market in the United States because they have been associated with rare, but sometimes fatal, side effects. The other major family, sulfonylureas, are presently sold under approximately 100 different brand names, and as a family, constitute the only oral hypoglycemic agent in widespread use at this time in the United States. Sulfonylureas, however, fail to control hypoglycemia on initial use in approximately 30 percent to 40 percent of new cases (primary failures), and in an additional 1 to 5 percent of the new cases, they eventually lose their effectiveness (secondary failures).

There are also a variety of natural products which appear to exhibit hypoglycemic activity. These products are generally plants or plant-derived compounds, usually in the form of a somewhat crude extract. It is estimated that more than 200 species of plants exhibit hypoglycemic properties, including many common plants, such as immature bean pods, olive leaves, potatoes, wheat, celery, blackberry leaves, sugar beets, and the leaves and roots of bananas (Farnsworth and Segelman, *Tile Till* 57:52–55, 1971).

Other potential hypoglycemic agents have been isolated, for example, from the leaves of *Aloe Aboraescens Var Natalis* (Hikino et el., *Int. J. Crude Drug Res.* 24:183–186, 1986) and from the roots of *Oryza-Sativa* (Hikino et al., *Planta Med. O:*490–492, 1986). In addition, studies in India have shown that leaf extracts of *Gynema sylvestre* can prolong the life span of Alloxan-induced diabetic rats. However, use of these extracts in intact animals leads to highly variable results. These extracts also induce hypoglycemia in the Alloxan model (Srivastava et el., *Int. J. Crude Drug. Res.* 24:171–176, 1986).

The seeds of *Eugenia Jambolana,* another plant found in India, appear to exhibit hypoglycemic activity comparable to that of chlorpropamide, as determined by effects on cathepsin B (Bansal et al., *Indian J. Biochem. Biophy.* 18:377, 1981). Further, it has been reported that *Salvia lavandulifolia* possesses a slight hypoglycemic activity that is independent of the effects of insulin (Jimenez et al., *Planta Med.* 1:260–262, 1986). Other folklore remedies, including tea made from herbs such as *Allofylus edulis* (Barboza et al., *Plantas Que Curan,* 1985), *Daucus carota* and *Catharanthus roseus,* have been sold for the control of diabetes in South American or Southeast Asian countries.

Due to the lack of consistent clinical effectiveness for previously suggested synthetic oral hypoglycemic agents, there is a need in the art for additional, safe, oral hypoglycemic agents that provide the clinician with a wider range of options in managing maturity onset NIDDM. The present invention fills this need, and further provides other related advantages.

SUMMARY OF THE INVENTION

Briefly stated, the present invention provides a variety of hypoglycemic agents for use in the maintenance of maturity onset non-insulin dependent diabetes mellitus (NIDDM). In one aspect of the present invention the hypoglycemic agent comprises a polar solvent extract of at least one part of the plant *Hexachlymus edulis* or related Hexachlymus species. The part may include the leaves, seed pods, roots or bark of the plant. Within a preferred embodiment, the polar solvent extract is an alkynol or aqueous alkynol extract. Particularly preferred is an aqueous ethanol extract.

A method for preparing the polar solvent extract hypoglycemic agents briefly described above is also provided. The method comprises (a) macerating at least one part of the plant *Hexachlymus edulis,* or related Hexachlymus species, with a polar solvent to yield a solution and solid plant debris; and (b) separating the solution from the solid plant debris, thereby yielding an extract suitable as a hypoglycemic agent.

Another aspect of the present invention is directed toward a method for reducing the blood glucose level in a patient, comprising administering to the patient an effective amount of a composition comprising a polar solvent extract of at least one part of the plant *Hexachlymus edulis* or related Hexachlymus species, in combination with a physiologically acceptable carrier or diluent. Suitable carriers or diluents include alcohol, water, physiological saline, dimethyl sulfoxide, and mixtures thereof.

Another aspect of the present invention provides a method for reducing symptomatic conditions associated with diabetes in a patient, such as polydipsia, polyuria and polyphagia. The method comprises administering to the patient an effective amount of a composition comprising a polar solvent extract of at least one part of the plant *Hexachlymus edulis* or related Hexachlymus species, in combination with a physiologically acceptable carrier or diluent.

The present invention is also directed toward methods for preparing hypoglycemic agents from *Hexachlymus edulis* or related Hexachlymus species by cell culture. In one embodiment, the method comprises (a) preparing a callus from explants of seedlings or plant cuttings of the plant *Hexachlymus edulis* or related Hexachlymus species; (b) culturing one or more cells from the callus; and (c) separating a fraction containing hypoglycemic activity from the culture medium, thereby yielding a fraction suitable as a hypoglycemic agent. In another embodiment, the method comprises (a) infecting cuttings from seedlings of the plant *Hexachlymus edulis* or related Hexachlymus species with a plant pathogen capable of cell transformation; (b) culturing one or more infected seedling cells; and (c) separating a fraction containing hypoglycemic activity from the cultured cells, thereby yielding a fraction suitable as a hypoglycemic agent.

Another aspect of the present invention is also directed toward a method for reducing the blood glucose level in a patient. The method comprises administering to the patient an effective amount of a composition comprising a hypoglycemic agent prepared according to the cell culture methods briefly described above, in combination with a physiologically acceptable carrier or diluent.

A related aspect of the present invention is also directed toward a method for reducing symptomatic conditions associated with diabetes in a patient, such as polydipsia, polyuria and polyphagia. The method comprises administering to the patient an effective amount of a composition comprising a hypoglycemic agent prepared according to the cell culture methods briefly described above, in combination with a physiologically acceptable carrier or diluent.

These and other aspects of the present invention will become evident upon reference to the following detailed description.

DETAILED DESCRIPTION OF THE INVENTION

As noted above, the present invention is directed toward the use of certain hypoglycemic agents derived from at least one portion of the plant *Hexachlymus edulis* (*H. edulis*) or related Hexachlymus species. Because there are a number of common names for *H. edulis* and they vary according to the region and language spoken, "*H. edulis*" as used herein includes all common names, such as Yva'hai, Ibajai and Cereja do Rio Grande.

*H. edulis* and related Hexachlymus species are bush-like plants which reach the size of a small tree when fully grown. They grow between 5 to 12 meters high with a dap of 25 to 70 centimeters. The tree-top is globose with abundant, tortuous ramification, while the trunk is straight and cylindrical. The lust or main shaft is 2 to 6 meters in length. The plants are heliotropes, which grow abundantly in the eastern region of Paraguay as well as along the Paraguayan River and the Parana River. They are also found in humid areas along the jungle border and in other open areas.

The plant can be generally identified by the following characteristics: (a) leaves that grow in opposite pairs, elliptical in shape and aromatic with translucent tips; (b) external bark which is dark brown in color with longitudinal groves forming short, rib-like lines; (c) inner bark which is a slight pink color; and (d) fruit which is spherical, yellow, the outer skin of which usually contains fuzz and has an unpleasant odor. The following is a more specific botanical description of *H. edulis:*

Bark—the outer bark is rough, hard, with longitudinal grooves forming short, rib-like lines. The color is dark brown. The bark is 3 to 6 millimeters thick. The inner barks color varies from light pink to light brown, with the color changing to dark red at the outer edges. The inner bark is 10 to 20 millimeters thick.

Leaves—the leaves grow in opposite pairs and their shape is elliptical, ranging from between 3 to 8 centimeters and 1 to 3 centimeters wide. The leaves also have long, translucent tips and smooth, rounded edges. The young leaves have fuzz which disappears with age. When the leaves are crushed, they emit an unpleasant odor characteristic of the plant.

Flowers and Fruit—the flowers are singular, white, 1.5 to 2.0 centimeters wide, with five petals and numerous stamen. The fruit is categorized as a drupe, subglobose in shape and yellow in color with fuzz. The fruit is between 3 to 6 centimeters in diameter, with five sharp-pointed fuzzy sepals which are attached at the apex. The fruit is edible, but very sour and acidic. There are one to two seeds in each fruit. The plants generally flower during June and September and fructify between September and November.

A hypoglycemic agent may be prepared from one or more parts, i.e., leaves, seed pods, roots or bark, of *H. edulis* or related Hexachlymus species. Although dry-stored, but not desiccated, leaves may be used, fresh leaves are preferred. A suitable method for preparing such an agent includes macerating at least one part of the plant with a polar solvent, preferably at room temperature and with occasional stirring, for from 1 hour to 45 days to yield a highly colored solution and solid plant debris. A 7-day time period for the extraction is preferred. Following maceration, although not essential, it is preferable to separate the solution from the solid plant debris. For example, the solution may be filtered to effectuate removal of the solid plant debris.

In general, and as partially discussed above, suitable polar solvent extracts may be prepared utilizing a number of methods that result in the basic separation of the constituents of interest from the remaining plant material. Suitable polar solvents include alkynols, phenols, acetonitrile, tetrahydrofuran, chlorinated hydrocarbons, and aqueous mixtures thereof. A preferred polar solvent is an alkynol or aqueous mixture thereof ("aqueous alkynol"). As used herein, "alkynols" include straight-chain and branched-chain alkyl alcohols, such as methanol, ethanol, propanol, and isopropanol. Particularly preferred is aqueous ethanol. Alkynol extracts from the seed pods and root materials appear to be more potent than similar leaf extracts.

Prior to the step of macerating, it may be desirable to physically disrupt the part of the plant that is utilized. It will be evident to those skilled in the art that there are a variety of ways in which the plant may be prepared prior to extraction as described within the present invention. For instance, the leaves, seed pods, roots or bark may be chopped, crushed or ground to increase the surface area exposed to the polar solvent.

The agents of the present invention may be administered to patients in a variety of forms and by a variety of routes. Irrespective of the form of the composition and the route of the administration, it is preferable that a regular dosage regime, i.e., daily, be maintained, as well as an appropriate diet.

As noted above, the present invention provides a method for reducing the blood glucose level in a patient that comprises administering to the patient an effective amount of a composition comprising a polar solvent extract of at least one part of the plant *Hexachlymus edulis* or related Hexachlymus species, in combination with a physiologically acceptable carrier or diluent. Physiologically acceptable carriers and diluents include alcohols, water, physiological saline, dimethyl sulfoxide (DMS), and mixtures thereof. The polar solvent extract may be administered by a variety of routes, including orally and transdermally. For oral administration, aqueous alcohol is a preferred diluent, and aqueous ethanol is particularly preferred. For transdermal administration, DMSO is a preferred carrier.

The effective and safe dosage range in humans appears to be wide. In clinical studies with 39 patients having maturity onset diabetes, no episodes of hypoglycemia were reported. Oral dosages of a polar solvent leaf extract that have been effective in lowering blood glucose levels in humans without hypoglycemic side effects range typically from about 0.25 ml to about 15 ml of the polar solvent leaf extract which has been diluted 10-fold with water or physiological saline. These dosages were administered daily. A preferred dosage of the polar solvent leaf extract is about 1.5 ml to 5 ml per day. Daily oral dosages of a polar solvent seed extract range typically from about 0.1 ml to 5 ml when diluted 10-fold with water or physiological saline. A preferred dosage of the polar solvent seed extract is about 0.5 ml to 2 ml per day. On a dry weight basis, these dosages are estimated to range from approximately 10 milligrams to several hundred milligrams per day. Higher dosages may be indicated for extracts in cases of very high blood glucose levels (300 mg/dl range) By way of comparison, dosages of Diabenise® (chlorpropamide) are generally held in the 100–250 mg per day range to avoid hypoglycemic side effects.

In healthy rats, the dosage range (in milligrams per kilogram body weight) required to effect a 30% decrease in blood glucose levels appeared to be higher than that required to lower glucose levels in hyperglycemic humans. Rats were treated with daily dosages as high as 80 mg/kg body weight (administered twice daily) to effect the 30% decrease, whereas human dosages were in the 1 to 20 mg/kg body weight range. By way of comparison, chlorpropamide dosages are in the 1 to 3 mg/kg body weight range for humans.

Treatment of patients with the aqueous ethanol extract has resulted in the successful management of NIDDM, even where other oral hypoglycemic agents have failed. For instance, the aqueous ethanol extract succeeded in several patients where sulfonylureas, such as chlorpropamide, had failed.

Yet another aspect of the present invention provides a method for reducing symptomatic conditions associated with diabetes in a patient. Symptomatic conditions include polydipsia, polyuria and polyphagia. The polar extract compositions described within the present invention, when administered to a patient, appeared to effectuate a reduction in the symptomatic conditions associated with diabetes prior to a reduction in blood glucose levels.

One method for reducing symptomatic conditions comprises administering to the patient an effective amount of a composition comprising a polar solvent extract of at least one part of the plant *Hexachlymus edulis* or related Hexachlymus species, in combination with a physiologically acceptable carrier or diluent. Preferred parts of the plant include leaves, seed pods, roots and bark. Suitable polar solvents include those described above. A preferred polar solvent is an alkynol or aqueous mixture thereof. Particularly preferred is aqueous ethanol. Suitable routes of administration and acceptable carriers and diluents are described above. Typical and preferred dosages, as well as suitable concentrations, are also described above.

As noted above, the present invention provides methods for preparing hypoglycemic agents by culturing plant cells derived from *H. edulis* or related Hexachlymus species. Briefly, seeds are collected from *H. edulis* trees in the wild. After seeds are stored at approximately 4° C. for three to four weeks, the fibrous husks are carefully removed so as not to damage the seed itself. Seed damage may be determined by appearance, within 6–8 hours, of a dark red color at the site of injury. Seeds are then sterilized with a 2.5% solution of sodium hypochloride in water. After this treatment, seeds are intercalated between several layers of household paper towels, which are kept moist and maintained at room temperature under a grow light for 24 hours/day. Approximately half of the seeds prepared in this manner sprout within 4 weeks. Useable seedlings (plantlets) are generally obtained within 5 weeks. Subsequent fungal growth on the seeds may be controlled with a 10% solution of copper sulfate in water.

Seedlings of *H. edulis* may be used for the production of hypoglycemic agents via callus culture methodology or hairy root culture methodology. Callus formation from explants of the seedlings described above may be accomplished on agar media (e.g., according to the procedures of Tisserat, *Plant Cell Culture: A Practical Approach*, R. A. Dixon (ed.), IRL Press, Oxford, England, 1985). Alternatively, mature plant cuttings may be used in a similar manner for callus formation. Subsequent growth, e.g., in liquid suspension culture, of individual cells derived from the callus culture is also accomplished by well-known techniques (e.g., R. A. Dixon (ed.), *Plant Cell Culture: A Practical Approach*, 1985). It will be evident to those skilled in the art that the number of cells processed may be increased, e.g., using commercially available bioreactors.

A fraction containing hypoglycemic activity may be separated from the culture medium by a variety of ways. For example, where quantities sufficient for a particular purpose are secreted by the cells, a fraction containing hypoglycemic activity may be isolated from other components of the culture medium by techniques such as dialysis or gel filtration. Alternatively, an active fraction may be prepared by isolating and rupturing the cells, with or without extraction of the cells or lysate using a polar solvent. In order to increase the yield of hypoglycemic activity, it may be desirable to induce secondary metabolic production in the cultures. It will be evident to those skilled in the art that there are a variety of ways in which the cells may be induced prior to separation of a hypoglycemic fraction as described within the present invention. For example, the cells may be stressed using techniques which include heat and the withholding of essential nutrients such as nitrogen.

As noted above, seedlings of *H. edulis* may also be used for the production of hypoglycemic agents by the use of a transformed cell system known as hairy root culture. To initiate hairy root growth, cuttings from seedlings (plantlets) are infected with a plant pathogen capable of cell transformation. Preferred pathogens include *Agrobacterium rhyzogenes*. Such infection causes cell transformation in some of the explants, resulting in rapidly growing tissue that take on the appearance of the small hairy roots normally found in growing root organs. These organized cell systems can proliferate on agar nutrient medium and may be induced to produce secondary metabolites. A fraction containing hypoglycemic activity may be separated from the cultured cells in a variety of ways, including physical disruption of isolated cells with or without extraction using a polar solvent. As described above for callus culture, the number of cells processed via hairy root systems may be increased, e.g., by the use of bioreactors.

The following examples are offered by way of illustration, and not by way of limitation.

EXAMPLE 1

A. Method of Preparation for Aqueous Ethanol Tincture

Aqueous ethanol extracts used in the clinical studies described herein were prepared by mixing 200 grams of finely ground *H. edulis* leaves with 1 liter of 35% alcohol in a tightly closed glass bottle. The mixture was allowed to stand for 15 days, the bottle shaken for 3 minutes once each day. On the 15th day, an additional 1 liter of 35% alcohol was added, bringing the total to 2 liters. The tightly closed bottle was then allowed to macerate for an additional 30 days, during which the bottle was shaken for 3 minutes each day. After a total of 45 days, the mixture was strained and allowed to slowly percolate 20 drops per minute for a minimum of 10 hours. The same method was used to prepare the active seed and root tinctures.

For human consumption, a water/alcohol solution of 1 part distilled water and 1 part alcohol (35%) was prepared. The final mixture was 1 part of the tincture extract to 9 parts of the water/alcohol solution (10-fold dilution).

B. Administration of Diluted Aqueous Ethanol Tincture

Patients were given between 20 and 30 drops (about 0.05 ml per drop) of the diluted aqueous ethanol tincture, administered under the tongue, 3 times per day, depending on the severity of their diabetic condition, one-half hour before each meal.

A 12-month clinical history of a patient treated with a polar solvent leaf alcohol extract (LAE) revealed a steady but gradual decline in the blood glucose over a period of about four months to a level within the normal range at which point it stabilizes.

Table 1 shows the reduction of blood glucose levels by a polar solvent seed alcohol extract (SAE).

TABLE 1

| Patient | Glucose Level Before SAE Treatment | Glucose Level After SAE Treatment |
| --- | --- | --- |
| CB | 110 | 110 |
| HC | 125 | 80 |
| LC | 200 | 136 |
| MC | 180 | 134 |
| EG | 154 | 105 |
| BL | 147 | 86 |
| AM | 155 | 135 |
| EM | 148 | 108 |
| CS | 230 | 140 |
| MU | 160 | 110 |

Glucose testing method—Hexoquinasa—mg/dl.

Table 2 is a comparison of the leaf and seed alkynol extracts in the control of blood glucose levels in ten patients suffering from NIDDM.

TABLE 2

| Patient | Before SAE Treatment (After LAE Treatment) Glucose Level | After SAE Treatment Glucose Level |
| --- | --- | --- |
| JM | 120 | 100 |
| IM | 145 | 120 |
| HC | 160 | 135 |
| CR | 180 | 125 |

TABLE 2-continued

| Patient | Before SAE Treatment (After LAE Treatment) Glucose Level | After SAE Treatment Glucose Level |
| --- | --- | --- |
| BM | 170 | 110 |
| AR | 110 | 100 |
| FG | 145 | 118 |
| JS | 130 | 90 |
| JB | 148 | 127 |
| MG | 134 | 87 |

Glucose testing method—Hexoquinasa in mg/dl.

The *H. edulis* polar solvent seed alcohol extract (SAE) proved to be 20% more effective in decreasing blood sugar levels as compared to results under the same conditions using the polar solvent leaf alcohol extract (LAE). There were no failures in the study. Based on the study, the SAE is estimated to be 50% more potent than the LAE.

A study was conducted wherein ten patients who had been on the *H. edulis* extract treatment for several months were divided into two groups of five each. One group was given a placebo, and the second group was retained on the *H. edulis* extract. Placebo patients were not informed, and were not aware of the change in their treatment. Within 3–4 days, all of the placebo patients reported the return of diabetic symptoms such as polyuria.

TABLE 3

Blood Glucose Measurements in Diabetic Patients Immediately Before Crossover and at Approximately 7 Days After Crossover Average Blood Glucose Levels (mg/dl)

| | Before Crossover | At 7 Days |
| --- | --- | --- |
| Placebo Group | 108 +/− 13 | 154 +/− 11 |
| Treatment Group | 103 +/− 11 | 103 +/− 11 |

Patients receiving the placebo experienced an approximate 43% increase in fasting blood glucose levels (see Table 3). Patients who remained on the extract showed no change in their average blood glucose levels at 7 days after crossover. None of these latter patients reported any diabetic symptoms during the study.

C. Summary of Human Clinical Results

Thirty-nine patients were treated with either the LAE or SAE extracts according to the following protocol. The human subjects in the studies were volunteers, and represent a cross section with regard to age, sex and clinical outlook. Each patient served as his or her own control, i.e., blood glucose levels were determined before and after treatment. Patients diagnosed as needing the agent were at or above the 180 mg/dl blood glucose level while fasting. Each patient was given the same amount of tea twice per day. All 39 patients were able to achieve and maintain preclinical blood glucose levels within 30 days. Polyuria, polyphagia, and polydipsia symptoms, when present, were alleviated within 1 to 3 days with SAE and within 7–15 days with LAE. Of these patients, at least 5 had previously been taking chlorpropamide, but were not able to attain preclinical blood sugar levels with this hypoglycemic agent. Over the four-year course of the studies using LAE and SAE extracts, there were no incidents of hypoglycemia and no primary failures. One secondary failure was observed.

EXAMPLE 2

Comparative Animal Studies

Both healthy and genetically diabetic mice, as well as healthy rats, have shown statistically significant decreases in blood glucose levels after treatment with an *H. edulis* extract. In these studies, both acute and sustained effects on blood glucose have been observed.

In one animal study, three preparations were evaluated. The test fractions were identified as (1) control, (2) chlorpropamide, and (3) an aqueous ethanol extract. Forty rats were divided into three treatment groups and were orally gavaged with 4–5 ml of the test materials twice each day. The blood glucose levels were measured after 1 and 2 weeks of study and are shown in Table 4.

TABLE 4

Blood Glucose Levels in Rat Studies
Blood Glucose (mg %)

| Sample | 7-Day | 15-Day |
| --- | --- | --- |
| Control | 93.7 | 111.0 |
| Chlorpropamide | 60.1 | 56.3 |
| Aqueous Ethanol Extract | 72.7 | 74.6 |

In a study using the db/db (diabetic) variant of the C-57 black mouse, 30 animals were divided into three groups of ten each. After fasting for 12 hours, Group I was gavaged with water, Group 2 with an aqueous solution containing 1 mg/ml of chlorpropamide and Group 3 with an *H. edulis* aqueous ethanol extract. Blood glucose levels were determined immediately prior to gavage and at one hour after gavage. Differences in levels induced by the extract were statistically significant by non-parametric tests.

Table 5 shows mean blood glucose levels for each of the groups before and after gavage.

TABLE 5

Blood Glucose Levels of db/db Mice Before
and One Hour After Gavage
Blood Glucose Levels (mg/dl)

| | Pre-Gavage | 1-Hour Post Gavage | Difference |
| --- | --- | --- | --- |
| Control | 390 +/− 37 | 357 +/− 36 | −33 |
| Chlorpropamide | 332 +/− 41 | 275 +/− 34 | −57 |
| H. edulis | 455 +/− 44 | 354 +/− 40 | −94 |

For the testing of fractions from the purification of the polar solvent extract, a modified bioassay using the female C57 B2/6 mouse was developed. The approach to the use of an animal model was to use the short recovery phase of the response rather than the longer initiation phase. The basic concept for the mode is to prime the animals for at least 2 weeks with the *H. edulis* aqueous ethanol extract ("ETOH extract"), which as described above has hypoglycemic activity. Once the hypoglycemic response is achieved, the animals are subgrouped (10 per group) and either maintained on the ETOH extract, removed from the ETOH extract and allowed to recover, or administered a test fraction of the ETOH extract for at least 24 hours. After an overnight fast, blood samples are collected and evaluated for blood glucose. A response similar to the recovery group would indicate the lack of hypoglycemic activity, whereas a response similar to the ETOH extract would suggest an active fraction. Hypoglycemic activity has been maintained in active fractions after separation through several steps (Table 6). In particular, the aqueous phase remaining after both the hexane and chloroform/ether extraction of the ETOH extract contained hypoglycemic activity similar to the ETOH extract itself, whereas the organic fraction showed no activity. When the chloroform/ether aqueous fraction was separated by ion exchange hypoglycemic activity was found in fractions wherein either the anions or the cations or both had been removed. Further separation using gel filtration and silica gels along with TLC were used to obtain active fractions that were analyzed as described in the chemical analysis section above.

TABLE 6

Hypoglycemic Activity of Fractions
Tested in the "Primed" Mouse Assay

| Chemical Separation | Fraction Tested | Blood Glucose mg/ml | | |
| --- | --- | --- | --- | --- |
| | | TEST | ETOH | RECOVERY |
| Chloroform/ ether | Aqueous Phase | 82 ± 7* | 81 ± 8 | 105 ± 6 |
| | Organic Phase | 132 ± 8 | 101 ± 4 | 131 ± 1 |
| Ion Exchange | Neutral Fraction | 85 ± 2* | 87 ± 4 | 97 ± 5 |
| | Neutral + Anion Fraction | 77 ± 5* | 72 ± 2 | 85 ± 5 |
| Gel Filtration | P2 Fraction 1 | 69 ± 3* | 71 ± 5 | 79 ± 5 |
| | P2 Fraction 2 | 93 ± 3 | 83 ± 4 | 90 ± 4 |

*Fraction showing hypoglycemic activity.

From the foregoing, it will be evident that, although specific embodiments of the invention have been described herein for purposes of illustration, various modifications may be made without deviating from the spirit and scope of the invention.

We claim:

1. A hypoglycemic composition, comprising:
   a polar solvent extract of the leaves, seed pods, roots or bark of the plant *Hexachlymus edulis*, in combination with a physiologically acceptable carrier or diluent.

2. The composition of claim 1 wherein the polar solvent is an alkynol or an aqueous alkynol.

3. The composition of claim 2 wherein the alkynol is ethanol.

4. The composition of claim 1 wherein said carrier or diluent is selected from the group consisting of ethanol, water, physiological saline, dimethyl sulfoxide, and mixtures thereof.

5. A hypoglycemic composition, comprising:
   an ethanol extract, or an aqueous ethanol extract, of the leaves, seed pods, roots or bark of the plant *Hexachlymus edulis*.

6. A process for preparing a hypoglycemic agent, comprising:
   macerating the leaves, seed pods, roots or bark of the plant *Hexachlymus edulis* with a polar solvent.

7. A process for preparing a hypoglycemic agent, comprising:
   (a) macerating the leaves, seed pods, roots or bark of the plant *Hexachlymus edulis* with a polar solvent to yield a solution and solid plant debris; and (b) separating said solution from said solid plant debris, thereby yielding an extract suitable as a hypoglycemic agent.

8. The process of claim 7 wherein said polar solvent is an alkynol or an aqueous alkynol.

9. The process of claim 8 wherein said alkynol is ethanol.

10. The process of claim 7 including, prior to the step of macerating, physically disrupting the leaves, seed pods, roots or bark of the plant *Hexachlymus edulis*.

11. A method for reducing the blood glucose level in a patient, comprising:

administering to the patient an amount of a composition effective to reduce the patient's blood glucose level, said composition comprising a polar solvent extract of the leaves, seed pods, roots or bark of the plant *Hexachlymus edulis*, in combination with a physiologically acceptable carrier or diluent.

12. The method of claim 11 wherein said polar solvent is an alkynol or an aqueous alkynol.

13. The method of claim 12 wherein the alkynol is ethanol.

14. The method of claim 11 wherein the carrier or diluent is selected from the group consisting of ethanol, water, physiological saline, dimethyl sulfoxide, and mixtures thereof.

15. The method of claim 11 wherein the step of administering comprises orally administering 0.25 ml to 15 ml per day of a polar solvent leaf extract which has been diluted 10-fold with aqueous alcohol.

16. The method of claim 11 wherein the step of administering comprises orally administering 1.5 ml to 5 ml per day of a polar solvent leaf extract which has been diluted 10-fold with aqueous alcohol.

17. The method of claim 11 wherein the step of administering comprises orally administering 0.1 ml to 5 ml per day of a polar solvent seed extract which has been diluted 10-fold with aqueous alcohol.

18. The method of claim 11 wherein the step of administering comprises orally administering 0.5 ml to 2 ml per day of a polar solvent seed extract which has been diluted 10-fold with aqueous alcohol.

19. A method for reducing polydipsia, polyuria or polyphagia associated with diabetes in a patient, comprising:

administering to the patient an amount of a composition effective to reduce polydipsia, polyuria or polyphagia in the patient, said composition comprising a polar solvent extract of the leaves, seed pods, roots or bark of the *Hexachlymus edulis*, in combination with a physiologically acceptable carrier or diluent.

20. The method of claim 19 wherein the polar solvent is an alkynol or an aqueous alkynol.

21. The method of claim 20 wherein the alkynol is ethanol.

22. The method of claim 19 wherein the carrier or diluent is selected from the group consisting of ethanol, water, physiological saline, dimethyl sulfoxide, and mixtures thereof.

23. The method of claim 19 wherein the step of administering comprises orally administering 0.25 ml to 15 ml per day of a polar solvent leaf extract which has been diluted 10-fold with aqueous alcohol.

24. The method of claim 19 wherein the step of administering comprises orally administering 1.5 ml to 5 ml per day of a polar solvent leaf extract which has been diluted 10-fold with aqueous alcohol.

25. The method of claim 19 wherein the step of administering comprises orally administering 0.1 ml to 5 ml per day of a polar solvent seed extract which has been diluted 10-fold with aqueous alcohol.

26. The method of claim 19 wherein the step of administering comprises orally administering 0.5 ml to 2 ml per day of a polar solvent seed extract which has been diluted 10-fold with aqueous alcohol.

27. A process for preparing a hypoglycemic agent, comprising:

(a) preparing a callus from explants of seedlings or plant cuttings of the plant *Hexachlymus edulis*;

(b) culturing one or more cells from the callus; and (c) separating a fraction containing hypoglycemic activity from the culture medium, thereby yielding a fraction suitable as a hypoglycemic agent.

28. A hypoglycemic agent prepared by the process of claim 27.

29. A process for preparing a hypoglycemic agent, comprising:

(a) infecting cuttings from seedlings of the plant *Hexachlymus edulis* with a plant pathogen capable of cell transformation;

(b) culturing one or more infected seedling cells; and (c) separating a fraction containing hypoglycemic activity from the cultured cells, thereby yielding a fraction suitable as a hypoglycemic agent.

30. The process of claim 29 wherein the plant pathogen is an *Agrobacterium rhyzogene*.

31. A hypoglycemic agent prepared by the process of claim 29.

32. The process of claim 27 or 29, additionally comprising, after the step of culturing, stressing the cultures by heat or the withholding of essential nutrients.

33. A method for reducing the blood glucose level in a patient, comprising:

administering to the patient an amount of a composition effective to reduce the patient's blood glucose level, said composition comprising a hypoglycemic agent according to claims 28 or 31, in combination with a physiologically acceptable carrier or diluent.

34. A method for reducing polydipsia, polyuria or polyphagia associated with diabetes in a patient, comprising:

administering to the patient an amount of a composition effective to reduce polydipsia, polyuria or polyphagia in the patient, said composition comprising a hypoglycemic agent according to claims 28 or 31, in combination with a physiologically acceptable carrier or diluent.

35. The method of claim 33 wherein the carrier or diluent is selected from the group consisting of ethanol, water, physiological saline, dimethyl sulfoxide, and mixtures thereof.

36. The method of claim 34 wherein the carrier or diluent is selected from the group consisting of ethanol, water, physiological saline, dimethyl sulfoxide, and mixtures thereof.

* * * * *